United States Patent
Tsuruoka et al.

(10) Patent No.: US 11,598,724 B2
(45) Date of Patent: Mar. 7, 2023

(54) MEASURING APPARATUS, MEASURING APPARATUS ADJUSTMENT METHOD AND COMPUTER PROGRAM PRODUCT

(71) Applicant: SYSMEX CORPORATION, Kobe (JP)

(72) Inventors: Yasuaki Tsuruoka, Kobe (JP); Tomohiro Tsuji, Kobe (JP); Hiroo Tatsutani, Kobe (JP); Motoi Kinishi, Kobe (JP); Yuji Masuda, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 16/931,672

(22) Filed: Jul. 17, 2020

(65) Prior Publication Data
US 2021/0018438 A1 Jan. 21, 2021

(30) Foreign Application Priority Data
Jul. 18, 2019 (JP) .............................. JP2019-132474

(51) Int. Cl.
*G01N 21/64* (2006.01)
*G01J 3/28* (2006.01)
(Continued)

(52) U.S. Cl.
CPC ............ *G01N 21/6428* (2013.01); *G01J 3/28* (2013.01); *G01J 3/36* (2013.01); *G01J 3/4406* (2013.01);
(Continued)

(58) Field of Classification Search
CPC ....... G01N 21/6428; G01N 2021/6441; G01N 2201/1241; G01N 2015/1006;
(Continued)

(56) References Cited

U.S. PATENT DOCUMENTS

2004/0119974 A1* 6/2004 Bishop ............... G01N 21/6428
356/317
2006/0290929 A1* 12/2006 Imura ....................... G01J 3/28
356/328
(Continued)

FOREIGN PATENT DOCUMENTS

EP 1851545 A2 11/2007
JP 2004205508 A 7/2004
(Continued)

OTHER PUBLICATIONS

An Introduction to the Principles of FCM, VII. Pulse Processing System, 5. fluorescence correction—8. analog and digital methods, downloaded from the Internet "https://www.bc-cytometry.com/FCM/fcmprinciple_7-5.html#7-5-5" operated by Beckman Coulter, Inc. (6 pages).
(Continued)

*Primary Examiner* — Dominic J Bologna
(74) *Attorney, Agent, or Firm* — Buchanan, Ingersoll & Rooney PC (57) ABSTRACT

A measuring apparatus includes a flow cell through which a sample containing particles flows, a light source for irradiating light on the sample flowing through the flow cell, a fluorescence detector for detecting the fluorescence generated from the sample irradiated with light from the light source, and a control unit for flowing a positive control sample containing a fluorescent dye through the flow cell, measuring the fluorescence generated from the positive control sample irradiated by the light from the light source via the fluorescence detector, comparing the obtained measurement value and a reference value, and adjusting the detection sensitivity of the fluorescence detector according to the comparison result.

17 Claims, 10 Drawing Sheets

(51) Int. Cl.
    *G01J 3/36*         (2006.01)
    *G01J 3/44*         (2006.01)
    *G01N 15/10*       (2006.01)
    *G01N 21/27*       (2006.01)
    *G01N 15/14*       (2006.01)
    *G01N 33/58*       (2006.01)
    *G01N 21/53*       (2006.01)

(52) U.S. Cl.
    CPC ........ G01J 3/4412 (2013.01); G01N 15/1012 (2013.01); G01N 15/1436 (2013.01); G01N 15/1459 (2013.01); G01N 21/274 (2013.01); G01N 33/582 (2013.01); *G01N 21/532* (2013.01); *G01N 2015/1006* (2013.01); *G01N 2015/144* (2013.01); *G01N 2021/6419* (2013.01); *G01N 2021/6421* (2013.01); *G01N 2021/6441* (2013.01); *G01N 2201/1241* (2013.01)

(58) Field of Classification Search
    CPC ............. G01N 15/1012; G01N 21/274; G01N 21/532; G01N 15/1459; G01N 2021/6419; G01N 2021/6421; G01N 33/582; G01N 15/1436; G01N 2015/144; G01J 3/28; G01J 3/36; G01J 3/4412; G01J 3/4406
See application file for complete search history.

(56) References Cited

U.S. PATENT DOCUMENTS

| | | | |
|---|---|---|---|
| 2008/0194508 A1* | 8/2008 | Christensen | G01N 33/54393 514/44 R |
| 2009/0230291 A1* | 9/2009 | Sakazume | G01N 21/274 250/214 R |
| 2009/0316148 A1* | 12/2009 | Minato | G01J 3/28 356/317 |
| 2010/0120059 A1 | 5/2010 | Yan et al. | |
| 2010/0256943 A1* | 10/2010 | Donnenberg | G01J 3/10 702/104 |
| 2015/0276449 A1* | 10/2015 | Ito | G01F 1/6847 73/861.351 |

FOREIGN PATENT DOCUMENTS

| | | |
|---|---|---|
| JP | 5529505 B2 | 6/2014 |
| WO | 2006/090283 A2 | 8/2006 |

OTHER PUBLICATIONS

Extended European Search Report dated Nov. 23, 2020, issued by the European Patent Office in corresponding European Application No. 20185928.7-1020, (13 pages).

* cited by examiner

MEASURING APPARATUS, MEASURING APPARATUS ADJUSTMENT METHOD AND COMPUTER PROGRAM PRODUCT

CROSS REFERENCE TO RELATED APPLICATION

This application claims priority from prior Japanese Patent Application No. 2019-132474, filed on Jul. 18, 2019, entitled "MEASURING APPARATUS, MEASURING APPARATUS ADJUSTMENT METHOD AND PROGRAM", the entire contents of which are incorporated herein by reference.

FIELD OF THE INVENTION

The present invention relates to a measuring apparatus, a measuring apparatus adjustment method, and a computer program product.

BACKGROUND

Japanese Patent Application Publication No. 2004-205508 discloses a flow cytometer for irradiating a laser light on a fluorescence-labeled sample to measure the fluorescence generated from each cell. This flow cytometer is provided with a fluorescence detector corresponding to each fluorescent dye to be detected in order to detect the fluorescence from a plurality of fluorescent dyes having different spectra.

This flow cytometer uses a fluorescence detector such as a photomultiplier tube (PMT) or an avalanche diode capable of amplifying the detected signal in order to detect low level fluorescence. The detection sensitivity of each fluorescence detector, that is, the degree of signal amplification, is adjusted according to the fluorescent dye to be detected so that the measured value of the fluorescence from each cell falls within the dynamic range.

The signal amplification degree of the PMT is changed by adjusting the voltage applied to the PMT. In this flow cytometer, the PMT is set to a plurality of different applied voltages during setup, the fluorescence from the fluorescently labeled beads is measured at each applied voltage, and the linear functional relationship between the applied voltage and the output fluorescence value is experimentally determined and stored. Then, when the target fluorescence value is set for each PMT, the applied voltage that will output the target fluorescence value from the fluorescence detector is calculated using the determined functional relationship.

SUMMARY OF THE INVENTION

In the flow cytometer of Japanese Patent Application Publication No. 2004-205508, it is necessary to prepare the above-mentioned functional relationship for adjusting the detection sensitivity of PMT according to each PMT and fluorescent dye. Therefore, when a new PMT is used or a new fluorescent dye is used, in order to obtain the above-mentioned functional relationship corresponding to the machine differences (error due to individual differences of the device), it is necessary to obtain data by performing many new measurements.

The present invention relates to a measuring apparatus comprising: a flow cell through which a sample containing particles flows; a light source to irradiate light on the sample flowing through the flow cell; a fluorescence detector to detect fluorescence generated from the sample irradiated with light from the light source; and a controller programmed to carry out a sensitivity adjustment comprising: causing a positive control sample containing a fluorescent dye to flow through the flow cell, obtaining a measurement value of the fluorescence generated from the positive control sample irradiated by the light from the light source via the fluorescence detector, comparing the measurement value and a reference value, and adjusting a sensitivity of the fluorescence detector according to a comparison result.

The present invention relates to a method for adjusting measuring apparatus comprising: flowing a positive control sample containing a fluorescent dye through a flow cell; irradiating the positive control sample flowing through the flow cell with light; measuring the fluorescence generated from the positive control sample irradiated with light by a fluorescence detector to obtain a measurement value; comparing the measurement value with a reference value; and adjusting a sensitivity of the fluorescence detector according to the comparison result.

The present invention relates to a computer program product, comprising: a computer hardware storage device having stored therein computer usable program code for adjusting a measuring apparatus, the computer usable program code, which when executed by a computer hardware system in a measuring apparatus, causes the measuring apparatus to perform: flowing a positive control sample containing a fluorescent dye through a flow cell; irradiating the positive control sample flowing through the flow cell with light; measuring the fluorescence generated from the positive control sample irradiated with light by a fluorescence detector to obtain a measurement value; comparing the measurement value with a reference value; and adjusting a sensitivity of the fluorescence detector according to the comparison result.

According to the measuring apparatus, the method for adjusting measuring apparatus, and the computer program product of the present invention, the detection sensitivity used for detecting light from a sample can be easily adjusted.

DESCRIPTION OF THE EMBODIMENT OF THE INVENTION

Hereinafter, embodiment will be described with reference to the drawings.

Figure 1A:
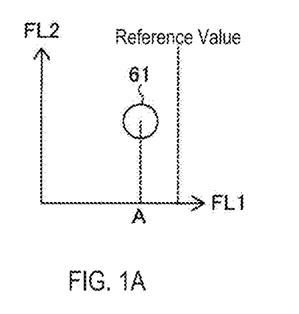
FIGS. 1A and 1B are schematic diagrams describing an outline of a sensitivity adjustment method of a fluorescence detector of a measuring apparatus.
Figure 1B:
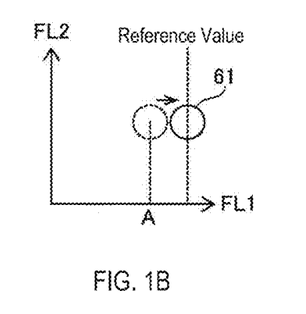

FIG. 1A and FIG. 1B are schematic views summarizing the sensitivity adjustment method of the fluorescence detector of the measuring apparatus. Described below is a case of measuring a positive control sample containing a bead population labeled with a predetermined amount of fluorescein isothiocyante (hereinafter, FITC bead population) in a flow cytometer provided with a PE detector for detecting the fluorescent dye phycoerythrin (hereinafter, PE) and a FITC detector for detecting the fluorescent dye fluorescein isothiocyanate (hereinafter FITC). In FIG. 1A and FIG. 1B show the dot-plotted appearance of the fluorescence intensity obtained from each bead by measuring a positive control sample containing an FITC bead population, wherein a fluorescence intensity (FL1) based on the output of the FITC detector is set on the horizontal axis, and a fluorescence intensity (FL2) based on the output of the PE detector is set on the vertical axis. As shown in FIG. 1A, the measurement result of the FITC bead population of the positive control sample is represented as a measurement value group 61. The measuring apparatus compares a statistical value A (for example, the median value of the fluorescence intensity) of the fluorescence intensity (FL1) generated from the FITC bead population and a reference value, and adjusts the detection sensitivity of the FITC detector so that the statistical value A is substantially equal to the reference value in accordance with the comparison result, as shown in FIG. 1B.

The detection sensitivity used for detecting the light from the sample can be easily adjusted by carrying out such an adjustment method.

Details of This Embodiment

Figure 2:
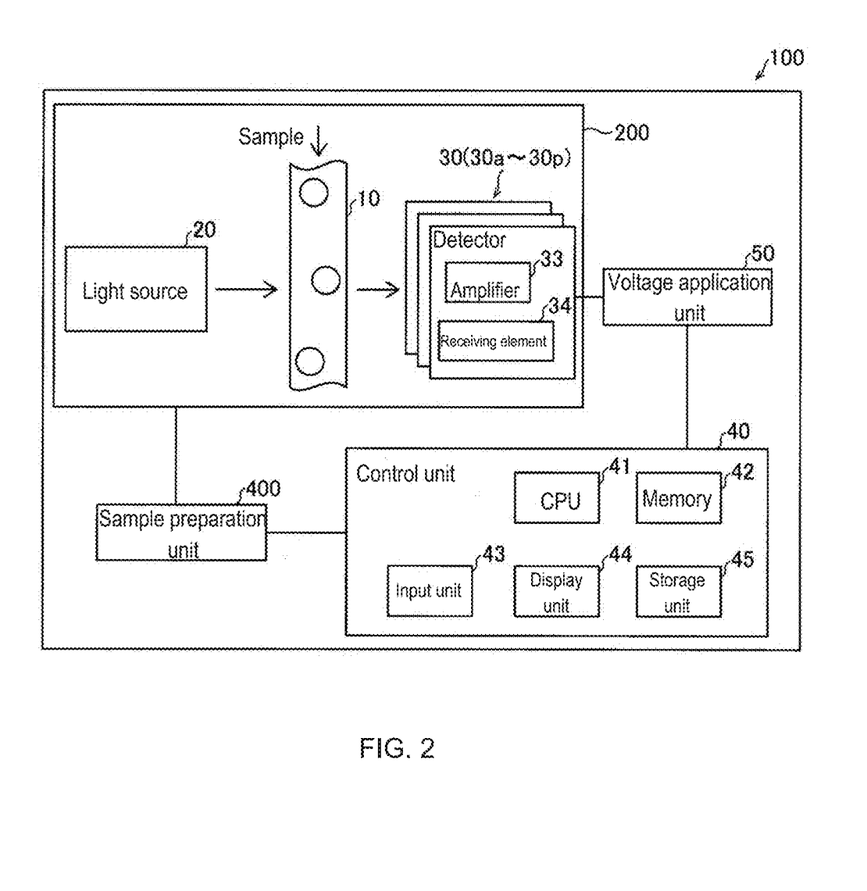
FIG. 2 is a block diagram for illustrating a measuring apparatus.

The measuring apparatus 100 will be described with reference to FIG. 2. The measuring apparatus 100 is a multi-color flow cytometer. The flow cytometer optically measures a sample by a flow cytometric method. The measuring apparatus 100 includes an optical system unit 200, a sample preparation unit 400, a voltage application unit 50, and a control unit 40.

The control unit 40 controls the operations of the optical system unit 200, the sample preparation unit 400, and the voltage application unit 50. The control unit 40 is a computer and includes a CPU (Central Processing Unit) 41, a memory 42, an input unit 43, a display unit 44, and a storage unit 45.

The CPU 41 performs the control process by the control unit 40. The memory 42 is used as a work area for performing the control process by the CPU 41. The memory 42 includes a RAM (Random Access Memory). The input unit 43 receives instructions input from the user. The input unit 43 also reads the information attached to the sample container. The input unit 43 includes, for example, a keyboard, a mouse, and a reader such as a barcode or RFID. The display unit 44 displays the measurement result of the optical system unit 200. The display unit 44 also displays screens for operations. The storage unit 45 stores a program for processing, measurement results, and information for measurement. The storage unit 45 is a ROM (Read Only Memory) is included.

The sample preparation unit 400 mixes a fluorescent reagent into the sample to be measured, labels the sample with a fluorescent dye, and prepares a sample suitable for measurement by the optical system unit 200.

The optical system unit 200 includes a flow cell 10, a light source 20, and a plurality of detectors 30 (30a to 30p). The detector 30 includes a light receiving element 34 that outputs an electric signal corresponding to the intensity of the detected light, and an amplification unit 33 that amplifies the electric signal output from the light receiving element 34. The detector 30 used for fluorescence detection is a photomultiplier tube (PMT), the light receiving element 34 includes a photocathode, and the amplification unit 33 includes a dynode.

Figure 3:
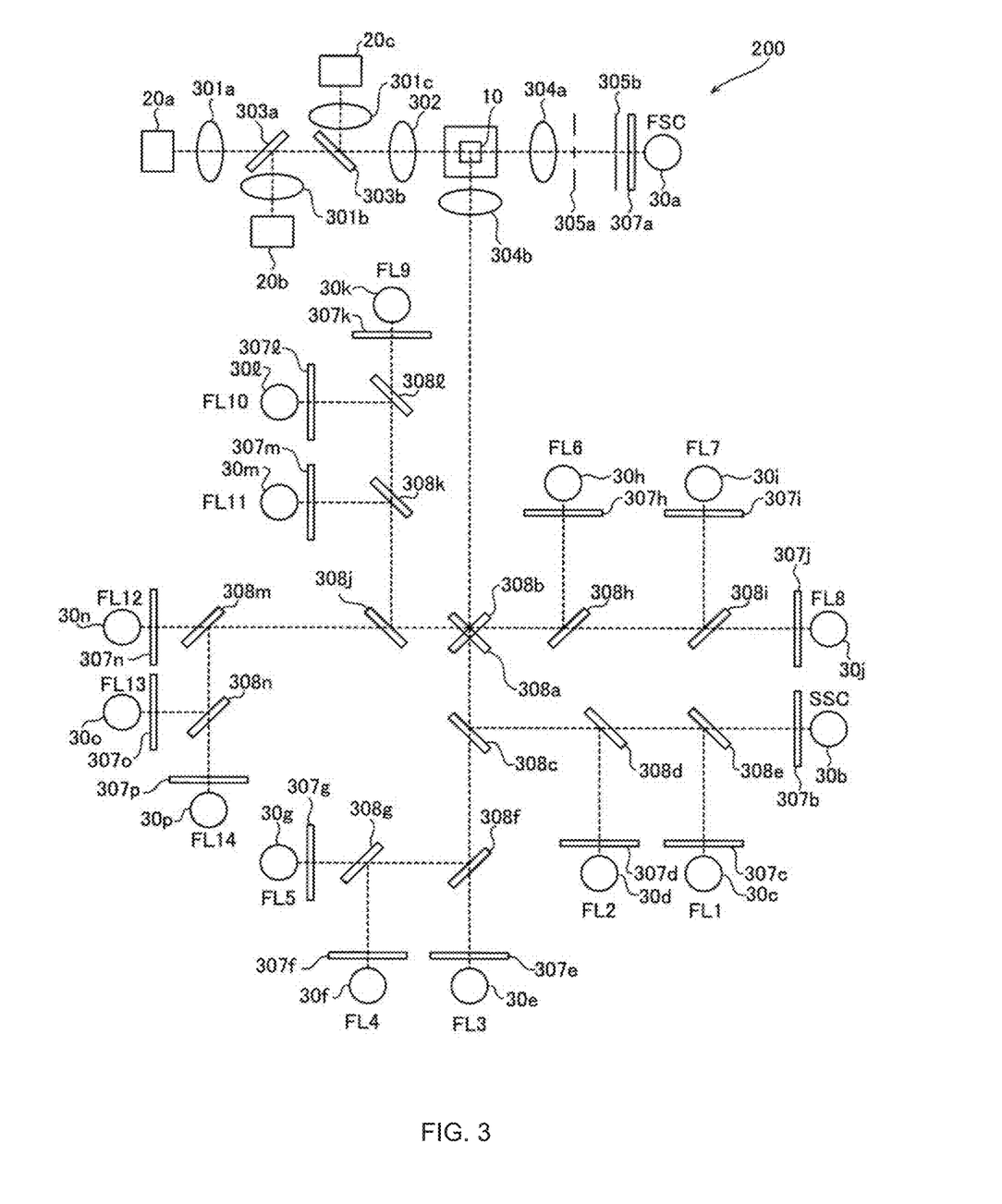
FIG. 3 is a diagram for describing an optical system of the measuring apparatus.

The optical system unit 200 will be described in more detail with reference to FIG. 3. The optical system unit 200 includes the flow cell 10, light sources 20a, 20b, and 20c, and detectors 30a to 30p. The flow cell 10 receives the sample prepared by the sample preparation unit 400. The light sources 20a to 20c irradiate light on the sample passing through the flow cell 10. The detectors 30a to 30p detect light from the sample and output a detection signal converted into an electric signal. The detector 30a is a detector that detects forward scattered light, and the detector 30b is a detector that detects side scattered light. The detector 30a and the detector 30b are photodiodes. The detectors 30c, 30d, 30e, 30f, 30g, 30h, 30i, 30j, 30k, 30l, 30m, 30n, 30o, and 30p are detectors that detect fluorescence. The detectors 30c to 30p are photomultiplier tubes (PMT). The detectors 30c to 30p have different fluorescent dyes to be detected. The PMT includes a photocathode, a dynode, and an anode. The photoelectrons generated by the photocathode are amplified by the dynode and output from the anode. The detection sensitivity of each of the detectors 30c to 30p is adjusted by changing the voltage applied to the dynode. That is, the light receiving element 34 shown in FIG. 2 includes a photocathode, and the amplification unit 33 includes a dynode. The voltage application unit 50 applies a voltage of a designated magnitude to the dynodes of the detectors 30c to 30p based on instruction from the control unit 40.

The light sources 20a to 20c emit light having different wavelengths. The light source 20a emits light having a wavelength of about 488 nm. The light source 20b emits light having a wavelength of about 642 nm. The light source 20c emits light having a wavelength of about 405 nm. The light emitted from the light source 20a passes through a collimator lens a, dichroic mirrors 303a and 303b, and a condenser lens 302, and is applied to the flow cell 10. The light emitted from the light source 20b is transmitted through a collimator lens b, reflected by the dichroic mirror 303a, transmitted through the dichroic mirror 303b, transmitted through the condensing lens 302, and emitted to the flow cell 10. The light emitted from the light source 20c passes through a collimator lens c, reflected by the dichroic mirror 303b, passes through the condenser lens 302, and is emitted to the flow cell 10.

The forward scattered light of the light originating from the sample passing through the flow cell 10 passes through a condenser lens 304a, a beam stopper 305a, a pinhole plate 305b, and a bandpass filter 307a, and enters the detector 30a.

The side scattered light and fluorescent light originating from the particles contained in the sample passing through the flow cell 10 are condensed by a condenser lens 304b. The side scattered light incident on the detector 30b passes through dichroic mirrors 308a and 308b from the condenser lens 304b, then is reflected by a dichroic mirror 308c, passes through dichroic mirrors 308d and 308e, and the bandpass filter 307b, and is incident on the detector 30b.

The fluorescence incident on each of the detectors 30c to 30p is divided into mutually different wavelength bands by the dichroic mirrors 308a to 308n. The fluorescence incident on the detector 30c passes through the dichroic mirrors 308a and 308b from the condenser lens 304b, then is reflected by the dichroic mirror 308c, transmitted through the dichroic mirror 308d, reflected by the dichroic mirror 308e, and transmitted through the bandpass filter 307c, whereupon the light enters the detector 30c. The fluorescence incident on the detector 30d passes through the dichroic mirrors 308a and 308b from the condenser lens 304b, then is reflected by the dichroic mirror 308c, reflected by the dichroic mirror 308d, and transmitted through the bandpass filter 307d, whereupon the light enters the detector 30d.

The fluorescence incident on the detector 30e passes through the dichroic mirrors 308a, 308b, 308c, and 308f from the condenser lens 304b, then passes through the bandpass filter 307e, whereupon the light enters the detector 30e. The fluorescence incident on the detector 30f passes through the dichroic mirrors 308a, 308b, and 308c from the condenser lens 304b, then is reflected by the dichroic mirror 308f, reflected by the dichroic mirror 308g, transmitted through the bandpass filter 307f, whereupon the light enters the detector 30f.

The fluorescence incident on the detector 30g passes through the dichroic mirrors 308a, 308b and 308c from the condenser lens 304b, then is reflected by the dichroic mirror 308f, passes through the dichroic mirror 308g and the band pass filter 307g, whereupon the light enters the detector 30g. The fluorescence incident on the detector 30h is reflected from the condensing lens 304b to the dichroic mirror 308a, transmitted through the dichroic mirror 308b, reflected by the dichroic mirror 308h, transmitted through the bandpass filter 307h, whereupon the light enters the detector 30h.

The fluorescence incident on the detector 30i is reflected from the condenser lens 304b to the dichroic mirror 308a, transmitted through the dichroic mirrors 308b and 308h, reflected by the dichroic mirror 308i, transmitted through the bandpass filter 307i, whereupon the light enters the detector 30i. The fluorescence incident on the detector 30j is reflected from the condenser lens 304b to the dichroic mirror 308a, transmitted through the dichroic mirrors 308b, 308h and 308i, transmitted through the bandpass filter 307j, whereupon the light enters the detector 30j.

The fluorescence incident to the detector 30k is reflected from the condenser lens 304b to the dichroic mirror 308b, transmitted through the dichroic mirror 308a, reflected by the dichroic mirror 308j, transmitted through the dichroic mirrors 308k, 308l, and the bandpass filter 307k, whereupon the light enters the detector 30k. The fluorescence incident on the detector is reflected from the condensing lens 304b to the dichroic mirror 308b, transmitted through the dichroic mirror 308a, reflected by the dichroic mirror 308j, transmitted through the dichroic mirror 308k, and reflected by the dichroic mirror 308l, passes through the pass filter 307l, whereupon the light enters the detector 30l.

The fluorescence incident on the detector 30m is reflected from the condenser lens 304b to the dichroic mirror 308b, transmitted through the dichroic mirror 308a, reflected by the dichroic mirror 308j, reflected by the dichroic mirror 308k, and transmitted through the bandpass filter 307m, whereupon the light enters the detector 30m. The fluorescence incident on the detector 30n is reflected from the condenser lens 304b to the dichroic mirror 308b, transmitted through the dichroic mirror 308a, transmitted through the dichroic mirrors 308j and 308m and the bandpass filter 307n, whereupon the light enters the detector 30n.

The fluorescence incident on the detector 30o is reflected from the condenser lens 304b to the dichroic mirror 308b, transmitted through the dichroic mirror 308a, transmitted through the dichroic mirror 308j, reflected by the dichroic mirror 308m, reflected by the dichroic mirror 308n, passes through the bandpass filter 307o, whereupon the light enters the detector 30o. The fluorescence incident on the detector 30p is reflected from the condenser lens 304b to the dichroic mirror 308b, transmitted through the dichroic mirror 308a, transmitted through the dichroic mirror 308j, reflected by the dichroic mirror 308m, transmitted through the dichroic mirror 308n, and transmitted through the bandpass filter 307p, whereupon the light enters the detector 30p.

The respective detection signals output from the detectors 30a to 30p are transmitted to the control unit 40, the control unit 40 acquires parameters such as light intensity from the detection signals, and the sample is analyzed based on the acquired parameters.

The number of light sources 20 may be one, two, or four or more. Preferably, the flow cytometer is equipped with at least three light sources 20. The light source 20 is selected according to the wavelength range of the light originating from the sample. When there are two or more light sources 20, these light sources 20 preferably emit light having different peak wavelengths.

The number of photodiodes, dichroic mirrors, and bandpass filters may be changed according to the number of peak wavelengths of light originating from the sample. The types of photodiode, dichroic mirror, and bandpass filter may also be selected according to the peak wavelength or wavelength region of light originating from the sample and the fluorescence intensity.

The control unit 40 controls the optical system unit 200 to obtain and store appropriate optical information according to the antigen based on information relating to detection sensitivity when the detector 30 detects scattered light or fluorescence, information relating to fluorescence correction according to a combination of detected fluorescences, and information relating to gating for selecting a distribution region of a sample to be detected.

Adjustment process of Measuring Apparatus 100

The adjustment process of the measuring apparatus 100 will be described with reference to FIG. 4.

First, the process will be described for adjusting the detection sensitivity of the fluorescence detector (30c, 30d, 30e, 30f, 30g, 30h, 30i, 30j, 30k, 30l, 30m, 30n, 30o, and 30p) by the control unit 40 of the measuring apparatus 100. In the adjustment of the detection sensitivity, the detection sensitivity of each fluorescence detector is adjusted so that particles labeled with a fluorescent dye and unlabeled particles are reliably separated in the fluorescence measurement at a specific wavelength. Here, the sensitivity adjustment in the case of performing multi-color analysis by combining FITC and PE will be described by way of an example. The fluorescence of FITC is detected by the fluorescence detector 30c, and the fluorescence of PE is detected by the fluorescence detector 30d.

In step S1 of FIG. 4, the control unit 40 sets the reference value of the fluorescence intensity, which is the target of sensitivity adjustment, and the upper limit value and lower limit value of the voltage (hereinafter, PMT voltage) applied to the fluorescence detector 30c for the FITC fluorescence detector 30c. The reference value is a value at which the fluorescence intensity obtained from a positive control sample containing a bead population labeled with a predetermined amount of FITC is sufficiently higher than the fluorescence intensity from a negative control sample containing an unlabeled bead population. However, if the reference value is increased, the amplification factor of the noise signal also increases, so the setting is made within a range in which the effect of the amplified noise signal is small. The reference value is input by the user via the input unit 43.

The control unit 40 sets the PMT voltage such that a measurement value larger than the input reference value is output from the fluorescence detector 30c, as the initial value of the upper limit value. The control unit 40 also sets the PMT voltage such that a measurement value smaller than the input reference value is output from the fluorescence detector 30c, as the initial value of the lower limit value. In step S2, the control unit 40 performs controls to start supplying the positive control sample to the flow cell 10.

In step S3, the control unit 40 adjusts the detection sensitivity of the fluorescence detector 30c by adjusting the applied voltage (PMT voltage) to the fluorescence detector 30c for FITC.

The process of step S3 of FIG. 4 will be described with reference to FIG. 5.

Figure 5:
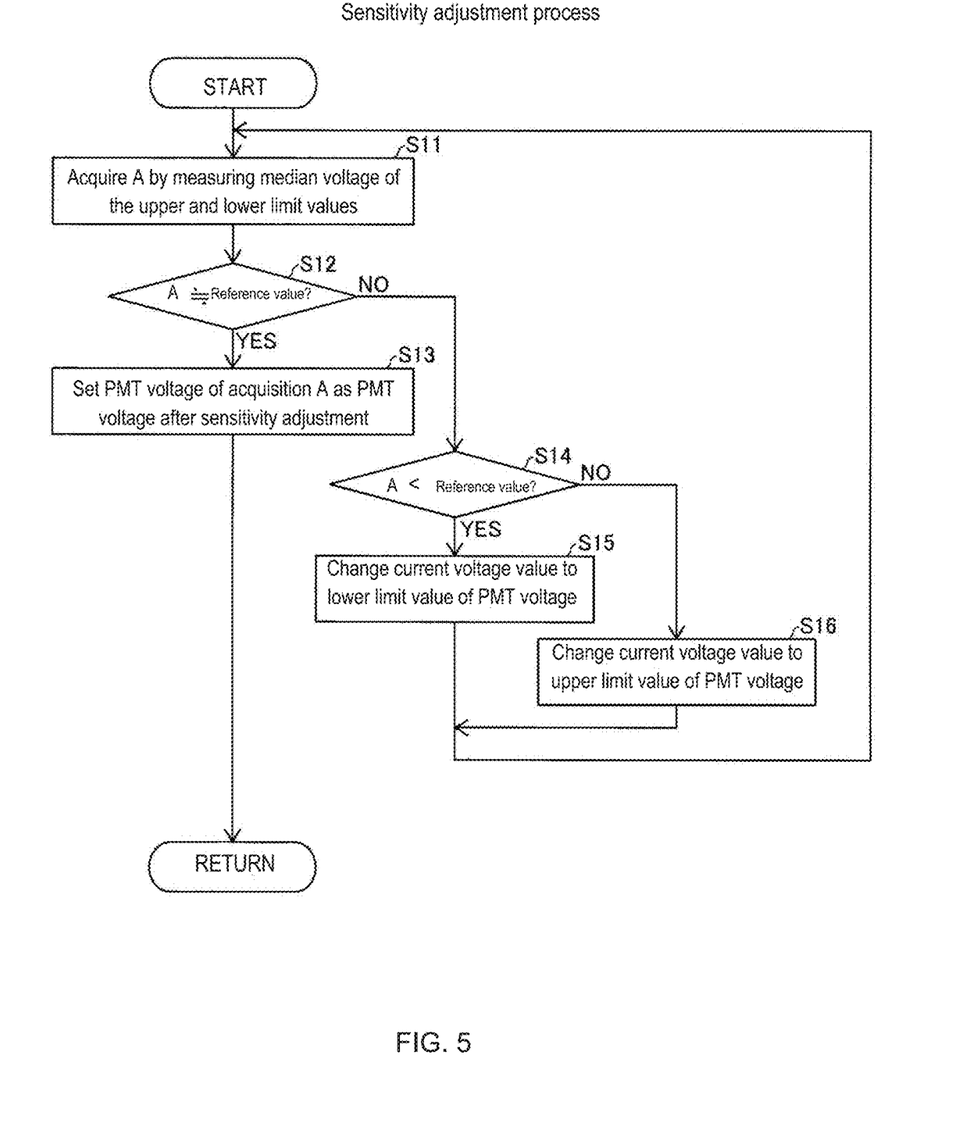
FIG. 5 is a flowchart describing the sensitivity adjustment process in step S3 of FIG. 4.

In step S11 of FIG. 5, the control unit 40 sets the median value of the upper limit value and the lower limit value as the PMT voltage of the fluorescence detector 30c, and measures the positive control sample. In this way the statistical value A of the fluorescence intensity obtained from the FITC bead population contained in the positive control sample is acquired. The median value of the fluorescence intensity obtained from each bead of the bead population is used as the statistical value A. In step S12, the control unit 40 compares the statistical value A with the reference value and determines whether the statistical value A is substantially equal to the reference value. That is, the control unit 40 determines whether the difference between the statistical value A and the reference value is within a predetermined range. When the difference between the statistical value A and the reference value is within the predetermined range, the process proceeds to step S13, whereas the process proceeds to step S14 when the difference between the statistical value A and the reference value is not within the predetermined range.

In step S13, the control unit 40 sets the PMT voltage at the time of obtaining the statistical value A as the PMT voltage after the sensitivity adjustment. Thereafter, the routine returns to the flowchart of FIG. 4. In step S14, the control unit 40 determines whether the statistical value A is smaller than the reference value. When the statistical value A is less than the reference value, the process proceeds to step S15, whereas the process proceeds to step S16 when the statistical value A is greater than the reference value.

Figure 4:
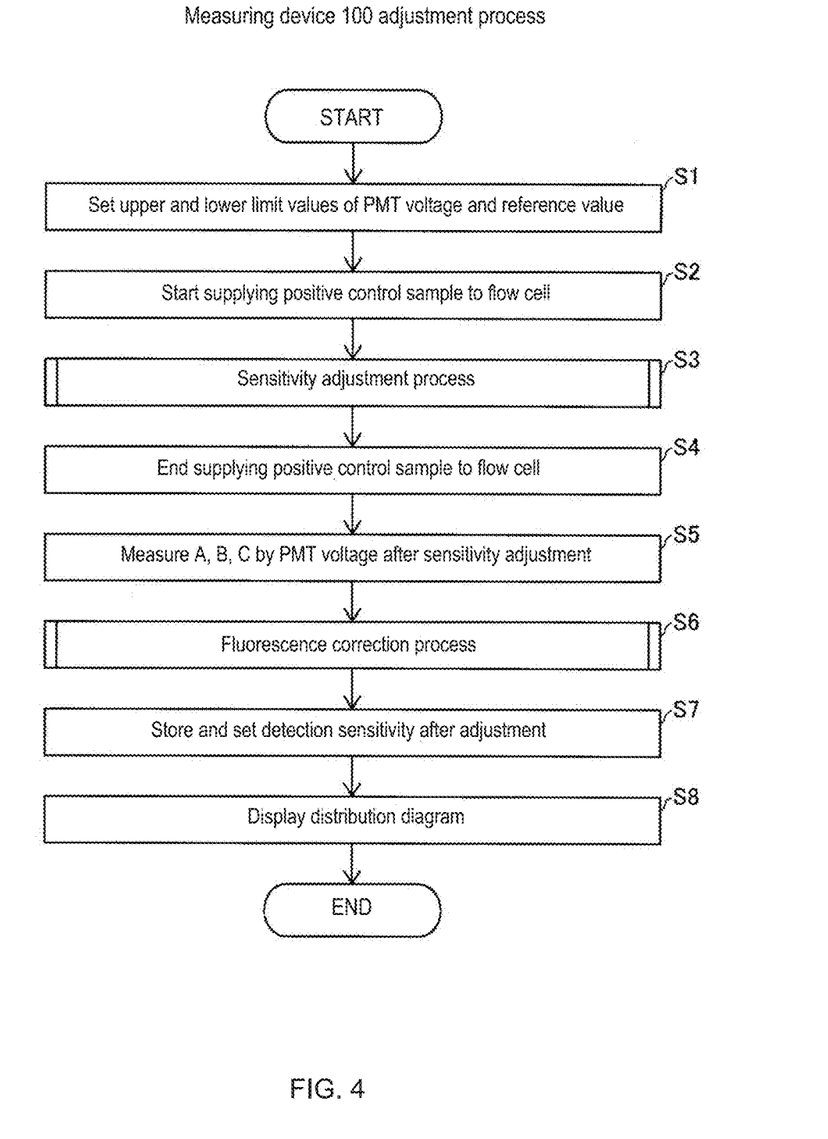
FIG. 4 is a flowchart describing an adjustment process of the measuring apparatus.

In step S15, the control unit 40 changes the current PMT voltage (the median value of the upper limit value and the lower limit value set in step S1 of FIG. 4) to the lower limit value of the PMT voltage. Thereafter, the routine returns to step S11. In step S16, the control unit 40 changes the current PMT voltage (the median value of the upper limit value and the lower limit value) to the upper limit value of the PMT voltage. Thereafter, the routine returns to step S11.

The sensitivity adjustment will be described in more detail with reference to FIGS. 6 and 7. The horizontal axis shows the fluorescence intensity (FL1) based on the output of the FITC fluorescence detector 30c, and the vertical axis shows the fluorescence intensity (FL2) based on the output of the PE fluorescence detector 30d. The measurement results of the FITC beads, which are the positive control beads, appeared as shown in the measurement value group 61. Hereinafter, an example in which the initial value of the lower limit value of the PMT voltage set in step S1 of FIG. 4 is 100 V and the initial value of the upper limit value is 1000 V will be described.

Figure 6A:
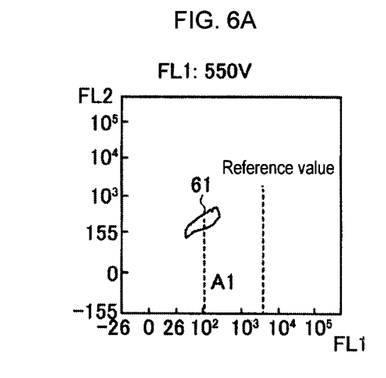
FIGS. 6A through 6E are diagrams showing an example of sensitivity adjustment of the measuring apparatus.
Figure 7:
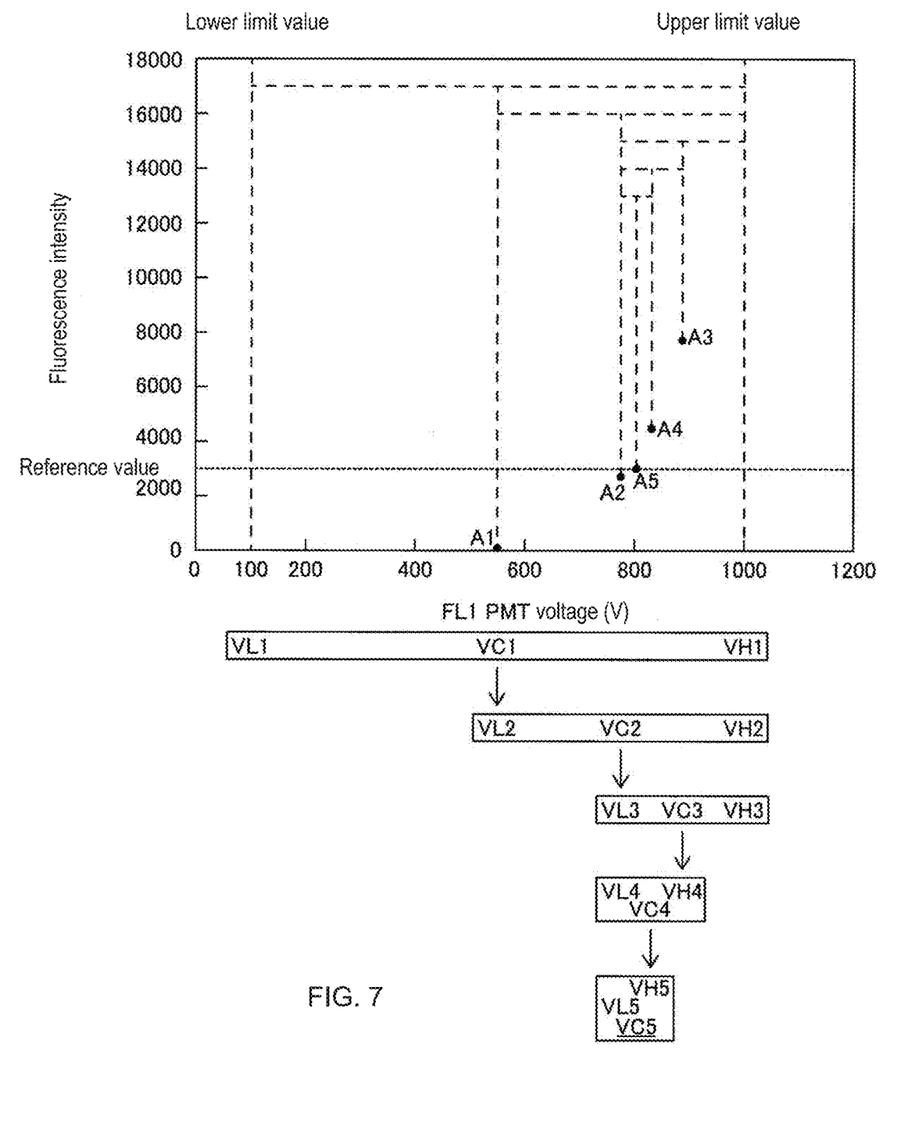
FIG. 7 is a diagram showing a relationship between voltage and fluorescence intensity in sensitivity adjustment of the measuring apparatus.

First, as shown in FIG. 7, the fluorescence intensity (FL1) of the positive control sample was measured by the median value VC1 (550V) of the lower limit value VL1 (100V) and the upper limit value VH1 (1000V) of the PMT voltage. As shown in FIG. 6A, when the PMT voltage is measured at 550 V, the statistical value A1 of the measurement value group 61 is smaller than the reference value, so the PMT voltage (550 V) used for the measurement is set to the next lower limit value.

Figure 6B:
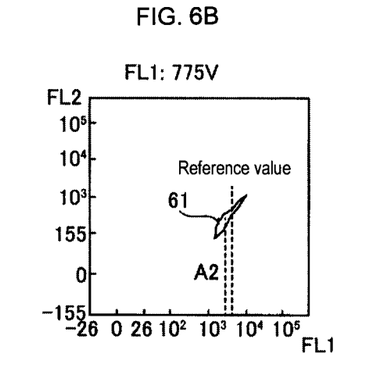

Next, as shown in FIG. 7, the fluorescence intensity (FL1) of the positive control sample was measured by the updated lower limit value VL2 (550V) of the PMT voltage and the median value VC2 (775V) of the upper limit value VH2 (1000V). As shown in FIG. 6B, when the PMT voltage is measured at 775 V, the statistical value A2 of the measurement value group 61 is smaller than the reference value, so the PMT voltage (775 V) used for the measurement is set to the next lower limit value.

Figure 6C:
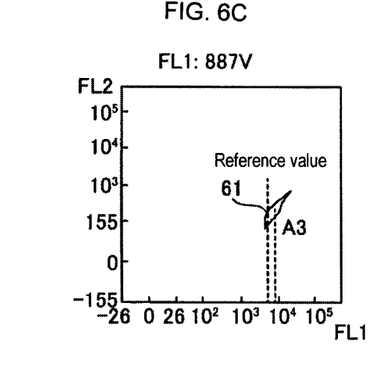

Next, as shown in FIG. 7, the fluorescence intensity (FL1) of the positive control sample was measured by the updated lower limit value VL3 (775 V) of the PMT voltage and the median value VC3 (887 V) of the upper limit value VH3 (1000 V). As shown in FIG. 6C, when the PMT voltage is 887 V, the statistical value A3 of the measurement value group 61 is larger than the reference value, so the PMT voltage (887 V) used for the measurement is set to the next upper limit value.

Figure 6D:
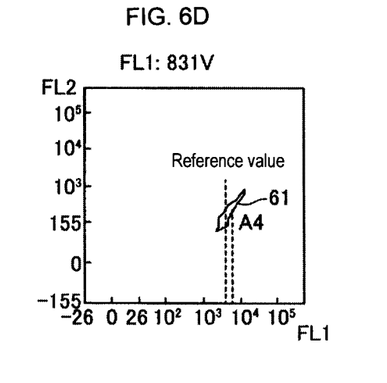

Next, as shown in FIG. 7, the fluorescence intensity (FL1) of the positive control sample was measured by the updated lower limit value VL4 (775 V) of the PMT voltage and the median value VC4 (831 V) of the upper limit value VH4 (887 V). As shown in FIG. 6D, when the PMT voltage is 831V, the statistical value A4 of the measurement value group 61 is larger than the reference value, so the PMT voltage (831V) used for the measurement is set to the next upper limit value.

Figure 6E:
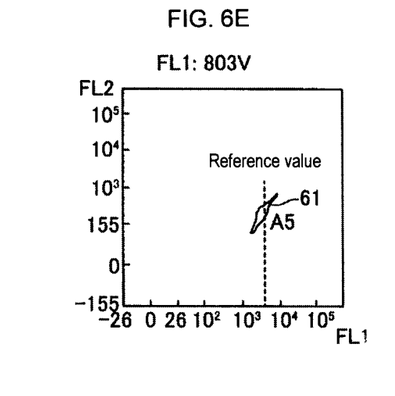

Next, as shown in FIG. 7, the fluorescence intensity (FL1) of the positive control sample was measured by the updated PMT voltage lower limit value VL5 (775 V) and the upper limit value VH5 (831 V) median value VC5 (803 V). As shown in FIG. 6E, when the PMT voltage is 803 V, the statistical value A5 of the measurement value group 61 is substantially equal to the reference value. In this way the sensitivity adjustment ends, and the process proceeds to step S4 in the flowchart of FIG. 4. Note that, in this embodiment, the condition that the statistical value A is substantially equal to the reference value is such that the difference between them is less than 5% of the reference value.

Note that, in the present embodiment, a binary search is used to search for the PMT voltage that matches the reference value. By the binary search method, it is possible quickly to search for an applied voltage that meets the conditions while narrowing the search range. As a result, the time it takes time to adjust the detection sensitivity of the fluorescence detector can be reduced. The search method also may be another search method. For example, the search method also may be linear search or bidirectional search.

Although the median value is used as the statistical value A, the mode value or the average value also may be used as the statistical value A.

Next, in step S4 of the flowchart of FIG. 4, the control unit 40 performs control for ending the supply of the positive control sample to the flow cell.

Next, in step S5, the control unit 40 measures the statistical value A of the fluorescence intensity of the FITC bead population in the positive control sample by the FITC fluorescence detector 30c after the detection sensitivity adjustment, measures the statistical value B of the fluorescence intensity of the FITC bead population in the same positive control sample by the PE fluorescence detector 30d after the detection sensitivity adjustment, measures the statistical value C of the fluorescence intensity of the bead population in the negative control sample by the PE fluorescence detector 30d after detection sensitivity adjustment, and stores the statistical values A, B, and C in the storage unit 45. These values are used in the fluorescence correction process in step S6. In this measurement, a mixed sample of the positive control sample and the negative control sample is supplied to the flow cell 10.

Next, in step S6, the control unit 40 performs a fluorescence correction process.

In a multi-color flow cytometer, a sample is multi-stained and fluorescences emitted from the plurality of fluorescent dyes is simultaneously detected. Since the fluorescence of each of the fluorescent dyes has a spectrum, the fluorescence emitted from the fluorescent dyes other than the fluorescent dye bound to the target molecule also may leak even when the fluorescent dyes are separated for each wavelength range by an optical system.

Figure 8:
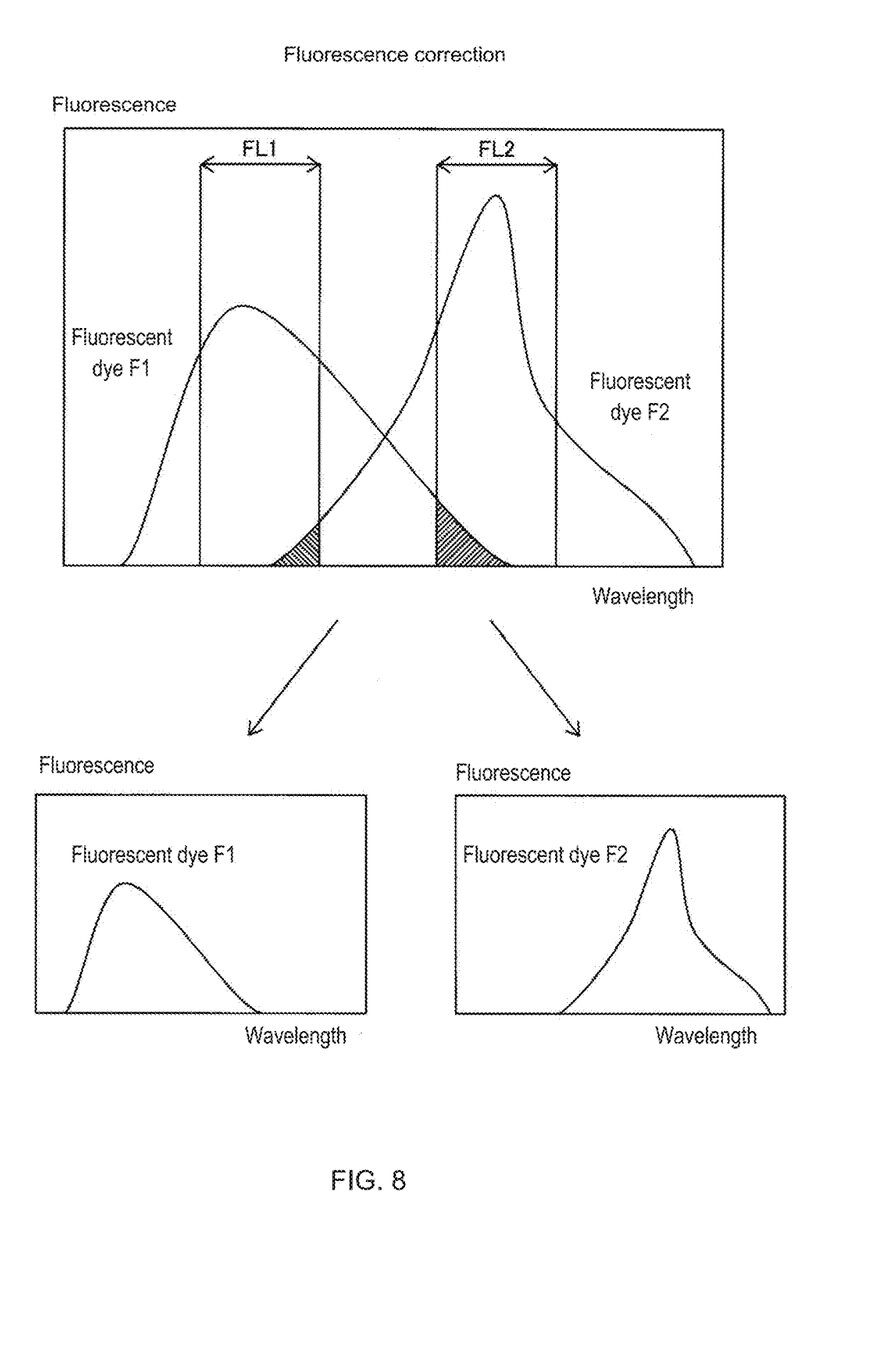
FIG. 8 is a diagram showing an outline of fluorescence correction of the measuring apparatus.

In the example shown in FIG. 8, a case where two fluorescences of the fluorescent dye F1 and the fluorescent dye F2 leak into each other will be considered. The fluorescent dye F1 is measured by detecting light in the wavelength range FL1. The fluorescent dye F2 is measured by detecting the light in the wavelength range FL2. A part of the fluorescence of the fluorescent dye F1 is included in the wavelength range FL2. A part of the fluorescence of the fluorescent dye F2 also is included in the wavelength range FL1. Therefore, the light from the fluorescent dye F1 can be detected by excluding the light from the fluorescent dye F2 in the detection of the light in the wavelength range FL1. The light of the fluorescent dye F2 also can be detected by excluding the light of the fluorescent dye F1 in the detection of the light in the wavelength range FL2.

The process of step S6 of FIG. 4 will be described with reference to FIG. 9. Here, a case will be described in which a fluorescence correction value for subtracting the fluorescence from FITC leaking into the fluorescence detector for PE is calculated.

Figure 9:
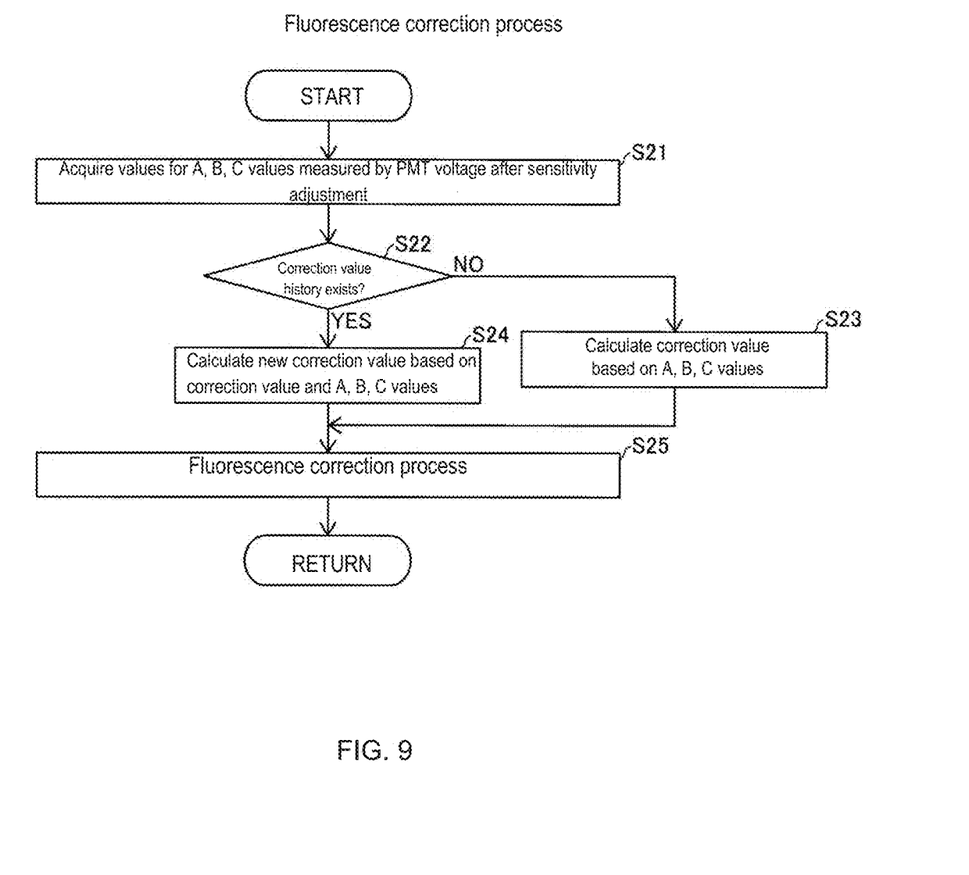
FIG. 9 is a flowchart showing the fluorescence correction process of step S6 of FIG. 5.

In step S21 of FIG. 9, the control unit 40 reads and stores the statistical values A, B, and C acquired in step S5 of FIG. 4, that is, statistic value A of the fluorescence intensity of the FITC bead population in the positive control sample measured by the FITC fluorescence detector 30c after detection sensitivity adjustment, statistic value B of the fluorescence intensity of the FITC bead population in the same positive control sample measured by PE fluorescence detector 30d after detection sensitivity adjustment, and statistical value C of fluorescence intensity of the bead population in the negative control sample measured by PE fluorescence detector 30d after detection sensitivity adjustment.

Here, the relationship matrix of the fluorescence correction can be expressed as shown in Expression (1).

Expression 1

$$\begin{bmatrix} 1 & tS_{12} \\ tS_{21} & 1 \end{bmatrix} \begin{bmatrix} tFL1 \\ tFL2 \end{bmatrix} = \begin{bmatrix} PMT1 \\ PMT2 \end{bmatrix} \qquad (1)$$

$tS_{21}$: Correction value for correcting leakage into the PE fluorescence detector by the FITC (correction value set last time or correction value initially set by user) $tS_{12}$: Correction value for correcting leakage of PE into the fluorescence detector for FITC (correction value set last time or correction value initially set by the user)

tFL1: Value regarded as true fluorescence intensity from FITC tFL2: value regarded as true fluorescence intensity from PE PMT1: Actual measurement value by the FITC fluorescence detector PMT2: Actual measurement value by the PE fluorescence detector Assuming that the fluorescence leakage has been removed by correction value $tS_{21}$, the statistical value A is substituted into tFL1 and the statistical value B is substituted into tFL2. The actual measurement value PMT2 from Expression (1) is expressed as Expression (2).

$$(TS_{21} \times A) + (1 \times B) = PMT2 \qquad (2)$$

In the case of the optimum fluorescence correction value, the relation matrix can be expressed as in Expression (3).

Expression 2

$$\begin{bmatrix} 1 & S_{12} \\ S_{21} & 1 \end{bmatrix} \begin{bmatrix} FL1 \\ FL2 \end{bmatrix} = \begin{bmatrix} PMT1 \\ PMT2 \end{bmatrix} \qquad (3)$$

$S_{21}$: Correction value for correcting leakage of FITC into the PE fluorescence detector $S_{12}$: Correction value for correcting leakage of PE into the FITC fluorescence detector FL1: True fluorescence intensity from FITC FL2: True fluorescence intensity from PE PMT1: Actual measurement value by the FITC fluorescence detector PMT2: Actual measurement value by the PE fluorescence detector In this case, there is no difference between the fluorescence intensity from the FITC bead population in the positive control sample measured by the PE fluorescence detector and the fluorescence intensity from the bead population in the negative control sample, hence, B=C. Then, the actual measurement value PMT2 from Expression (3) is expressed as Expression (4).

$$(S_{21} \times A) + (1 \times C) = PMT2 \qquad (4)$$

In Expressions (2) and (4), the measured values PMT2 are equal such that Expression (5) is derived.

$$(S_{21}A) + (1 \times C) = (TS_{21} \times A) + (1 \times B) \qquad (5)$$

Then, Expression (6) can be derived from Expression (5).

$$S_{21} = ((TS_{21} \times A) + (BC))/A \qquad (6)$$

Note that when setting the fluorescence correction value for the first time, $tS_{21}=0$. Therefore, $S_{21}=(BC)/A$. This $S_{21}$ value of is used as $tS_{21}$ at the next calculation.

In step S22, the control unit 40 confirms the history of the correction value $tS_{21}$ calculated using the same type of positive control sample and negative control sample or the correction value $tS_{21}$ initially set by the user. When there is no history of the correction value $tS_{21}$ and correction value $tS_{21}$ initially set by the user, the routine proceeds to step S23. On the other hand, when there is a history of the correction value tS21 or correction value $tS_{21}$ initially set by the user, the routine proceeds to step S24.

In step S23, the control unit 40 calculates the correction value $S_{21}$ to subtract the fluorescence from FITC value S for subtracting from FITC the fluorescence leaking into the fluorescence the PE fluorescence detector based on the above-mentioned statistical value A, statistical value B, and statistical value C. In step S24, the control unit 40 calculates a new correction value $tS_{21}$ based on the correction value $tS_{21}$ stored in the storage unit 45, and the statistical value A, the statistical value B, and the statistical value C.

As described above, in the fluorescence correction of subtracting the fluorescence from FITC for the PE fluorescence detector 30d, the control unit 40 calculates the correction value $S_{21}$ based on the value (B-C) related to the statistical value B of fluorescence intensity from the FITC bead population in the positive control sample measured by the PE fluorescence detector 30d, and the statistical value C of the fluorescence intensity from the bead population in the negative control sample.

In the above fluorescence correction, the control unit 40 calculates the correction value $S_{21}$ by accounting for the fluorescence intensity from the FITC bead population in the positive control sample measured by the FITC fluorescence detector.

Note that although the negative control is used to obtain the statistical value C in the present embodiment, the correction value $S_{21}$ also may be calculated with the statistical value C set as C=0 without using the negative control.

The controller 40 stores the calculated correction value $S_{21}$ in the storage unit 45. In this way the calculated correction value $S_{21}$ may easily be used in the calculation of the correction value $S_{21}$ or measuring the sample.

Figure 10A:
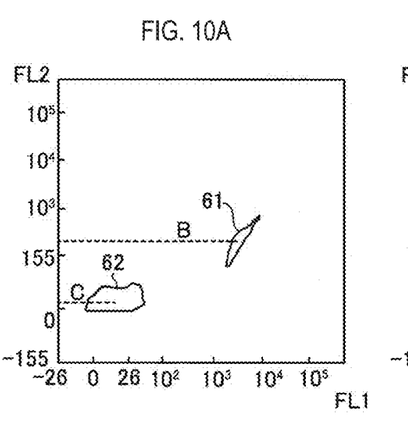
FIGS. 10A and 10B are diagrams showing an example of fluorescence correction of the measurement apparatus.
Figure 10B:
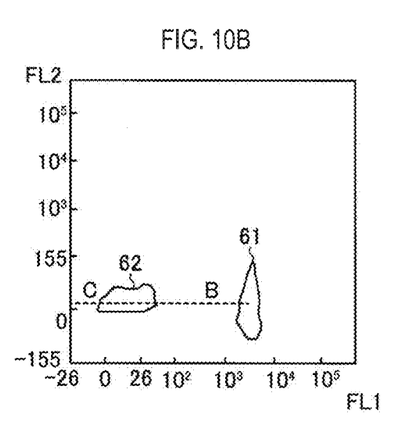
Figure 11:
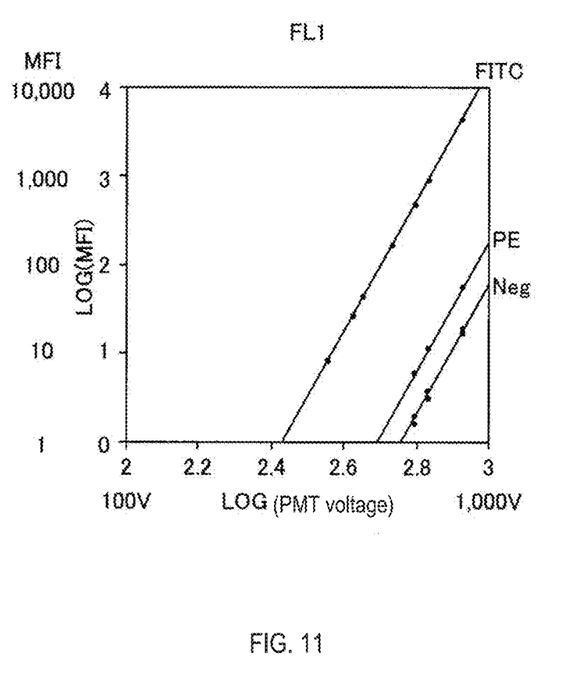
FIG. 11 is a block diagram showing a conventional fluorescence analyzer.

In step S25, the control unit 40 corrects statistical value B using the correction value $S_{21}$ as shown in FIGS. 10A and 10B. Then, the process proceeds to step S7 in the flowchart of FIG. 4.

In step S7, the control unit 40 stores the detection sensitivity of each fluorescence detector whose detection sensitivity has been adjusted in the storage unit 45. The control unit 40 sets the detection sensitivity of the fluorescence detector to the detection sensitivity stored in the storage unit 45 when measuring the sample collected from the subject.

In step S8, the control unit 40 displays on the display unit 44 a distribution chart (for example, the distribution chart shown in FIG. 6E) with the fluorescence intensity (FL1) and the fluorescence intensity (FL2) after detection sensitivity adjustment and fluorescence correction plotted as axes. In this way the user can check the distribution map to easily determine whether the calculation of the correction value $S_{21}$ and the sensitivity adjustment of the fluorescence detector has been performed correctly.

The measuring apparatus 100 also is configured to accept manual correction of the detection sensitivity and correction value $S_{21}$. For example, while the user is checking the distribution map, an operation can be performed to adjust the correction value $S_{21}$ and the like. This allows the user to check the distribution map and correct the detection sensitivity and the correction value $S_{21}$ more precisely so that the detection sensitivity and the correction value $S_{21}$ can be more accurately set.

Note that the embodiment disclosed this time are examples in all respects and not restrictive. The scope of the present invention is not restricted by the above description of the embodiment but by the scope of the claims, and includes meanings equivalent to the scope of the claims and all modifications (exemplary examples) therein.

For example, in the above embodiment, after the supply of the positive control is started in step S2 of the flowchart shown in FIG. 4 and the sensitivity control is completed in step S3, the supply of the positive control is terminated in step S4, and a mixture of the positive control and a negative control is supplied. The present invention is not limited to this sequence inasmuch as the supply of the mixed solution of the positive control and the negative control may be started in step S2, and the supply of the mixed solution may be terminated after the sensitivity adjustment processing of step S3 and the fluorescence correction processing of step S6 are completed. In this way the number of times the user supplies the control sample to the measuring apparatus can be reduced, and the adjustment work can be further simplified.

Although PMTs are used as the detectors 30c to 30p for detecting fluorescence in the above embodiment, avalanche photodiodes also may be used.

Although the detection sensitivity is adjusted by adjusting the voltage applied to the dynode of the PMT, the electric signal output from the detector also may be amplified by an amplifier circuit, or the electric signal output from the detector may be digitized and amplified by the control unit 40.

The sample to be measured by the measuring apparatus 100 is not limited to a sample containing cells collected from a subject, and may be a sample containing particles such as microorganisms, animal cells, plant cells, pollen, plankton, and the like.

Although a sample containing fluorescence-labeled beads is used as a positive control sample used for detection sensitivity adjustment, any sample that emits fluorescence may be used, for example, a measurement sample containing fluorescence-labeled cells may be used as a positive control sample. Moreover, the beads labeled with a fluorescent dye are not limited to the beads to which a fluorescent dye is directly bound, inasmuch as beads to which a fluorescent labeled antibody is bound also may be used. Beads with a fluorescent dye embedded therein also may be used. Similarly, the fluorescently labeled cells are not limited to cells to which a fluorescent dye is directly bound, inasmuch as cells to which a fluorescently labeled antibody is bound also may be used. Not only cells in which a fluorescent dye is bound to a cell surface antigen, but cells in which a fluorescent dye is bound to an antigen (cytokine or transcription factor) existing in the cytoplasm or nucleus also may be used. The target of fluorescent labeling is not limited to beads and cells, and may be any particle that can be fluorescently labeled. For example, a droplet containing DNA or cells to which a fluorescent dye is bound may be used as the fluorescently labeled particle.

What is claimed is:

1. A measuring apparatus comprising:
   a flow cell through which a sample containing particles flows;
   a light source to irradiate light on the sample flowing through the flow cell;
   a fluorescence detector to detect fluorescence generated from the sample irradiated with light from the light source; and
   a controller programmed to carry out a sensitivity adjustment comprising:
   (i) setting a sensitivity value of the fluorescence detector, the sensitivity value being within a value range defined by a lower limit and an upper limit,
   (ii) causing a positive control sample containing a fluorescent dye to flow through the flow cell,
   (iii) obtaining a measurement value of the fluorescence generated from the positive control sample irradiated by the light from the light source via the fluorescence detector set with the sensitivity value, (iv) comparing the measurement value and a reference value,
(v) determining whether a difference between the measured value and the reference value is smaller than a threshold value,
(vi) narrowing the value range when the difference is not smaller than the threshold value, wherein narrowing the value range includes:
  replacing the upper limit with the sensitivity value when the measured value is equal to or greater than the reference value; and
  replacing the lower limit with the sensitivity value when the measured value is smaller than the reference value,
(vii) repeating steps (i) to (vi) until the difference becomes smaller than the threshold value,
(viii) storing the sensitivity value in a storage unit when the difference is smaller than the threshold value.

2. The measuring apparatus according to claim 1, wherein
the positive control sample contains a plurality of particles labeled with a fluorescent dye; and
the controller obtains a value of the fluorescence generated from each particle in the positive control sample by the fluorescence detector to obtain, as the measurement value of the positive control sample, a statistical value calculated over the values of respective particles, and compares the statistical value with the reference value.

3. The measuring apparatus according to claim 2, wherein the statistical value is a median value, a mode value, or an average value of measured values obtained from each particle in the positive control sample.

4. The measuring apparatus according to claim 1, wherein the controller adjusts the sensitivity of the fluorescence detector by controlling a voltage applied to the fluorescence detector.

5. The measuring apparatus according to claim 4, wherein the fluorescence detector is configured to receive a fluorescence generated from the positive sample and output signal depending on the fluorescence and a voltage applied to the fluorescence detector, and
the controller obtains the measurement value based on the signal output from the fluorescence detector.

6. The measuring apparatus according to claim 5, wherein the controller applies a voltage within a range defined with an upper limit and a lower limit to the fluorescence detector, and the controller lowers the upper limit in response to the measurement value being higher than the reference value and raises the lower limit in response to the measurement value being lower than the reference value.

7. The measuring apparatus according to claim 5, wherein the controller repeats lowering and raising the upper and lower limits until the difference between the measurement value and the reference value is smaller than a threshold value.

8. The measuring apparatus according to claim 1, further comprising:
an input unit operated by a user;
wherein the controller sets a value input by the user via the input unit as the reference value.

9. The measuring apparatus according to claim 1, wherein the controller adjusts the sensitivity of the fluorescence detector by switching the detection sensitivity of the fluorescence detector while the positive control sample is flowing through the flow cell.

10. The measuring apparatus according to claim 1, wherein
the flow cell is configured to flow the sample containing particles that are multiply stained with the fluorescent dye and another fluorescent dye; and
the controller causes another positive control sample containing the other fluorescent dye to flow through the flow cell after adjusting the sensitivity of the fluorescence detector, obtains a measurement value of the fluorescence generated from the other positive control sample irradiated by the light source via the fluorescence detector, and determines a correction value for correcting leakage into the fluorescence detector due to fluorescence from the other fluorescent dye based on the measurement value.

11. The measuring apparatus according to claim 10, wherein
the controller causes a negative control sample free of fluorescent dye to flow through the flow cell after adjusting the sensitivity of the fluorescence detector, obtains a measurement value of the fluorescence generated from the negative control sample irradiated by light from the light source via the fluorescence detector, and determines the correction value based on a measurement value obtained from a negative control sample and the measurement value obtained from the other positive control sample.

12. The measuring apparatus according to claim 11, wherein
the controller causes a mixed sample of the negative control sample and the other positive control sample to flow through the flow cell.

13. A method for adjusting measuring apparatus comprising:
(i) setting a sensitivity value of a fluorescence detector, the sensitivity value being within a value range defined by a lower limit and an upper limit,
(ii) flowing a positive control sample containing a fluorescent dye through a flow cell;
(iii) irradiating the positive control sample flowing through the flow cell with light;
(iv) measuring the fluorescence generated from the positive control sample irradiated with light by a fluorescence detector to obtain a measurement value, the fluorescence detector being set with the sensitivity value;
(v) comparing the measurement value with a reference value;
(vi) determining whether a difference between the measured value and the reference value is smaller than a threshold value,
(vii) narrowing the value range and repeating steps (i) to (vi) until the difference becomes smaller than the threshold value, wherein narrowing the value range includes:
  replacing the upper limit with the sensitivity value when the measured value is equal to or greater than the reference value; and
  replacing the lower limit with the sensitivity value when the measured value is smaller than the reference value, and
(viii) storing the sensitivity value in a storage unit when the difference is smaller than the threshold value.

14. A computer program product, comprising:
a computer hardware storage device having stored therein computer usable program code for adjusting a measuring apparatus, the computer usable program code, which when executed by a computer hardware system in a measuring apparatus, causes the measuring apparatus to perform:
(i) setting a sensitivity value of a fluorescence detector, the sensitivity value being within a value range defined by a lower limit and an upper limit,
(ii) flowing a positive control sample containing a fluorescent dye through a flow cell;
(iii) irradiating the positive control sample flowing through the flow cell with light;
(iv) measuring the fluorescence generated from the positive control sample irradiated with light by a fluorescence detector to obtain a measurement value, the fluorescence detector being set with the sensitivity value;
(v) comparing the measurement value with a reference value;
(vi) determining whether a difference between the measured value and the reference value is smaller than a threshold value,
(vii) narrowing the value range when the difference is not smaller then the threshold value, wherein narrowing the value range includes:
replacing the upper limit with the sensitivity value when the measured value is equal to or greater than the reference value; and
replacing the lower limit with the sensitivity value when the measured value is smaller than the reference value,
(viii) repeating steps (i) to (vii) until the difference becomes smaller than the threshold value,
(ix) storing the sensitivity value in a storage unit when the difference is smaller than the threshold value.

15. The measuring apparatus according to claim 1, wherein
narrowing the value range includes replacing the upper limit or the lower limit with the sensitivity value.

16. The measuring apparatus according to claim 1, wherein
the sensitivity adjustment further comprises terminating flowing the positive control sample.

17. A method for adjusting measuring apparatus comprising:
(i) setting a voltage value of a photomultiplier tube, the voltage value being within a value range defined by a lower limit and an upper limit,
(ii) flowing a positive control sample containing a fluorescent dye through a flow cell;
(iii) irradiating the positive control sample flowing through the flow cell with light;
(iv) measuring the fluorescence generated from the positive control sample irradiated with light by a fluorescence detector to obtain a measurement value, the photomultiplier tube being set with the sensitivity value;
(v) comparing the measurement value with a reference value;
(vi) determining whether a difference between the measured value and the reference value is smaller than a threshold value,
(vii) narrowing the value range and repeating steps (i) to (vi) until the difference becomes smaller than the threshold value, and
(viii) storing the voltage value in a storage unit when the difference is smaller than the threshold value.

* * * * *